United States Patent

Tsibizov et al.

[11] 3,957,810
[45] May 18, 1976

[54] PHENANTHRO OXAZOLE PHOSPHOR COMPOUNDS

[76] Inventors: Jury Nikolaevich Tsibizov, Bulvar Mira 12, kv. 96, Nevinomyssk; Fedor Tikhonovich Pozharsky, ulitsa Engelsa, 81, kv. 8, Rostov-na-Donu; Andrei Mikhailovich Simonov, ulitsa Engelsa, 81, kv. 48, Rostov-na-Donu; Mikhail Isaakovich Knyazhansky, Universitetsky pereulok, 131 B, kv. 88, Rostov-na-Donu; Mikhail Borisovich Strjukov, ulitsa Engelsa, 34, kv. 30, Rostov-na-Donu, all of U.S.S.R.

[22] Filed: Sept. 24, 1973

[21] Appl. No.: 399,714

[52] U.S. Cl. .................. 260/307 D; 252/301.28
[51] Int. Cl.² ........................... C07D 263/52
[58] Field of Search ..................... 260/307 D

[56] References Cited
UNITED STATES PATENTS
3,257,204  6/1966  Sus et al. .................... 96/1.5

OTHER PUBLICATIONS
Stein et al., J.A.C.S. 64, pp. 2567–2569 (1942).

*Primary Examiner*—Raymond V. Rush
*Attorney, Agent, or Firm*—Haseltine, Lake & Waters

[57] ABSTRACT

Organic phosphors are essentially chemical compounds of the following structural formula

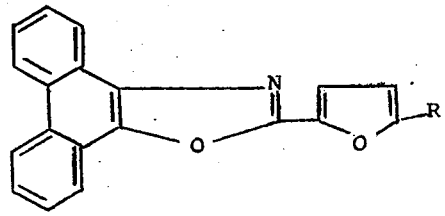

where R = H, Cl, Br, CHO, COCH$_3$, COOH, or

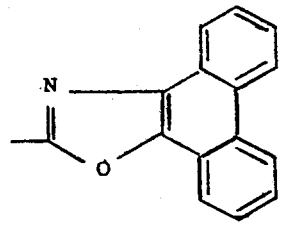

The method of preparing said substances resides in that 9,10-phenanthraquinonimine is made to react with 5-substituted furfural, wherein H, Cl, Br, CHO, COCH$_3$, COOH may be used as substituents in the presence of piperidine in a medium of an organic solvent at the reaction mixture boiling temperature, whereupon said solvent is eliminated.

1 Claim, No Drawings

PHENANTHRO OXAZOLE PHOSPHOR COMPOUNDS

The present invention relates to organic phosphors and methods of preparing same.

Said phosphors can be used in luminescent microscopy, flaw detection practice, for optical bleaching of cloth, or for preparing fluorescent dyes.

Known to be in current use are a number of organic phosphors based upon 2-furylbenzoxazole and having a melting point of 200° to 220°C (cf. Dutch Application No. 6,511,364 of 1966).

Organic phosphors of the structural formula

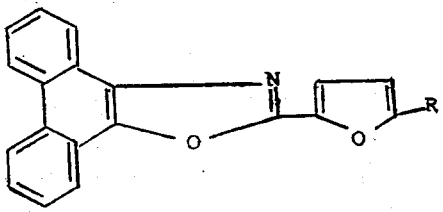

where R=H, Cl, Br, CHO, COCH$_3$, COOH, or

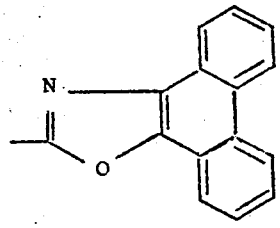

are obtained for the first time.

There exists a method of preparing 2-phenylphenanthro-/9,10/-oxazoles (cf. J. Am. Chem. Soc., 64, 2567 (1942). The method consists in reacting 9,10-phenanthrquinonimine with aromatic aldehydes in the presence of organic bases, such as piperidine, in a medium of an organic solvent at the reaction mixture boiling temperature, followed by isolation of the main product. No data are available in the literature on the application of compounds prepared by said method, as phosphors.

It is an essential object of the present invention to provide organic phosphors which are in effect the chemical compounds of the following structural formula:

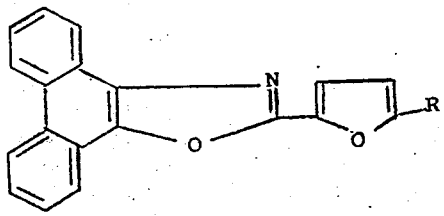

where R = Cl, Br, CHO, COCH$_3$, COOH, or

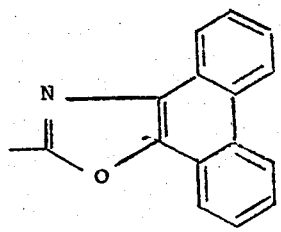

and develop a method for preparing same.

According to the invention, said compounds are provided.

The presence of the phenanthroxazole system in the resultant phosphors in combination with a variety of substituents in the furan ring makes is possible to obtain a reasonably long conjugated chain along the entire molecule of phosphor and vary the length of said chain, which in turn contributes to a broader spectral luminescence band, ranging from the violet to the greenish-blue.

According to the present invention, a method is developed of preparing said substances, which consists in reacting 9,10-phenanthroquinonmine with 5-substituted furfural, where Cl, Br, COOH, COCH$_3$, CHO may be used as substituents, in the presence of piperidine in a medium of an organic solvent at the reaction mixture boiling temperature, followed by the elimination of said solvent.

Under the thus-selected conditions the interreaction of 9,10-phenanthrenequinonemonoimine and 5-substituted furfural proceeds in the following sequence. First 9,10-phenanthraquinonmine is ionized with piperidine, resulting in the formation of the ion of quinoneimine which reacts with the C=O group of a heterocyclic aldehyde introduced into the reaction, with the formation of an intermediate compound and subsequent irreversible cyclization of the latter into the main product.

It is established that the yield of the main product is much affected by the quantity of piperidine introduced. Thus, piperidine introduction in an equimolar amount with respect to 9,10-phenanthraquinonimine increases the reaction time and reduces the yield of the main product, whereas the introduction of 1.8 to 2 piperidine moles per mole of 9,10-phenanthraquinonimine strongly reduces the reaction time and increases its yield. However, the isolation of the main product and its purification, in the case of introducing the aforesaid quantity of piperidine, are difficult to carry out due to high solvency of piperidine. Nevertheless, piperidine has to be taken in an amount somewhat exceeding the equimolar one as to 9,10-phenanthraquinonimine, since it leads to shifting the equilibrium towards the formation of ionized quinoneimine.

Thus, in order to obtain 2-(5'-substituted furyl-2')-phenanthro-/9,10/-oxazoles with Cl, Br, COCH$_3$, COOH, CHO as substituents in 5'-position, the interreaction process is recommended to be conducted with a molar ratio of 9,10-phenanthraquinonimine, 5-substituted furfural and piperidine equal to 1:1.2:1.2, respectively.

In order to obtain 2,5-(bisphenanthro-/9,10/-oxazolyl-2')-furan the interreaction process is recommended to occur with a molar ratio of 9,10-phenanthraquinonimine, 5-substituted furfural with the CHO group as a substituent, and piperidine equal to 2:1.2:2.4, respectively.

The yield of the main product is affected also by the sequence of introduction of the initial reagents. It is recommended that piperidine be introduced into the solution of 9,10-phenanthraquinonimine in an organic solvent with subsequent addition of the 5-substituted furfural, since with such a sequence the formation of by-products in minimized.

In case ethanol is used as an organic solvent, it is expedient, upon termination of the reaction, to eliminate 50 percent of its quantity initially used, since this increases the yield of the main product and facilitates its purification.

Organic phosphors which are in effect the chemical compounds of the following structural formula:

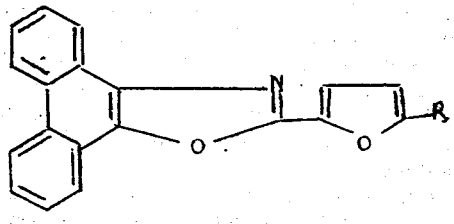

where R = H, Cl, Br, CHO, COCH$_3$, COOH, or

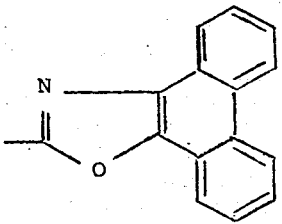

possess high quantum yield of luminescene (0.3 to 0.7), fairly high photostability, high melting point.

The process technique of the proposed method is simple since the reaction proceeds at atmospheric pressure and not very high temperatures. The reaction takes as little as two hours to proceed in a medium of conventional solvents, while isolation and purification of the reaction end products are carried out by commonly known methods. The main product prepared according to the proposed invention features a reasonably high yield of the order of 40 to 70 percent.

The herein-proposed method is carried into effect as follows.

A flask provided with a reflux condenser, is charged with a solution of 9,10-phenanthraquinonime in an organic solvent, such as ethanol, benzene, methanol, chloroform, whereupon added thereto are piperidine and 5-substituted furfural. The mixture is made to boil and allowed to stand in such a state for 0.5 to 2 hours. Upon termination of the reaction the solvent is eliminated from the reaction mixture and the main product is purified by the known methods.

For better understanding of the present invention, the following examples of the practical embodiment thereof are hereinafter given by way of illustration.

EXAMPLE 1

Preparing 2-(furyl-2')-phenanthro-/9,10/-oxazole

In a flask provided with a reflux condenser there are dissolved under heating 1 mmole of 9,10-phenanthraquinonimine in 20 ml of ethanol, followed by a consecutive addition of 1.2 mmole of piperidine and 1.2 mmole of furfural. The resultant mixture is subjected to boiling for 1.5 hours.

Upon termination of the reaction, 50-percent of the ethanol taking part in the reaction is distilled off from the reaction mixuure, and the remaining reaction mixture is cooled to let the main product settle down as a precipitate which is then filtered out, dried, dissolved in a minimum quantity of chloroform and purified by separating on a chromatographic column, with alumina as an adsorbent and UV light as an activator, the eluate being taken off from the zone luminescent with violet light. The eluate is then boiled with activated charcoal and filtered, whereupon petroleum ether is added to the eluate to precipitate the main product. The latter is recrystallized from dilute acetic acid to obtain colorless crystals of 2-(furyl-2')-phenanthro-/9,10/-oxazole.

Found, %: C, 79.78; H, 4.10; N, 5.01. Calculated, %: C, 80.00; H, 3.86; N, 4.91

EXAMPLE 2

Preparing 2-(5'-chlorofuryl-2')-phenanthro-/9,10/-oxazole

In a flask provided with a reflux condenser there are dissolved under heating 1 mmole of 9,10-phenanthraquinonime in 20 ml of benzene, whereupon there are added thereto consecutively 1.2 mmole of piperidine and 1.2 mmole of 5-chlorofurfural. The resultant mixture is boiled for 1.75 hours. Upon termination of the reaction the full amount of benzene is distilled off from the reaction mixture, the precipitated product is dissolved in a minimum quantity of chloroform and purified in manner similar to that described in Example 1 to obtain colorless crystals of 2-(5'-chlorofuryl-2')-phenanthro-/9, 10/-oxazole.

Found, %: C, 71.61; H, 3.29; N, 4.38 Calculated, %: C, 71.36; H, 3.13; N, 4.38

EXAMPLE 3

Preparing 2-(5'-bromofuryl-2')-phenanthro-/9,10/-oxazole

The experiment was conducted under the conditions of Example 1 with the sole exception that 5-bromofurfural was taken as the 5-substituted furfural. As a result, colorless crystals of 2-(5'-bromofuryl-2)-phenanthro-/9,10/-oxazole were obtained.

Found, %: C, 62.75; H, 2.94; N, 4.01. Calculated, %: C, 62.66; H, 2.75; N, 3.81

EXAMPLE 4

Preparing 2-(5'-formylfuryl-2')-phenanthro-/9,10/-oxazole

In a flask provided with a reflux condenser, there are dissolved under heating 1 mmole of 9,10-phenanthraquinonimine in 30 ml of ethanol, then there are added 1.2 mmole of piperidine and 1.2 mmole of 5-formylfurfural. The resultant mixture is boiled for 0.5 hour.

Upon termination of the reaction the reaction mixture is cooled, the precipitate is filtered out and the filtrate containing the main product, is concentrated by evaporation, dissolved in a minimum amount of chloroform and purified by thin-layer chromatography, by virtue of separating the yellow-colored alumina band and eluating the main reaction product therefrom by chloroform. Then the product is precipitated from the resultant solution with petroleum ether to obtain light-yellow crystals of 2-(5'-formylfuryl-2')-phenanthro-/9,10/-oxazole.

Found, %: C, 76.46; H, 3,29; N, 4.22 Calculated, %: C, 76.67; H, 3.51; N, 4.47

EXAMPLE 5

Preparing 2-(5'-acetylfuryl-2')-phenanthro-/9,10/-oxazole

The experiment was carried out under conditions of Example 1, the only exception being that 5-acetylfurfural was used as the 5-substituted furfural and that there was added to the obtained eluate an equivoluminal amount of petroleum ether, whereupon the resultant solution is evaporation-concentrated. Upon cooling the obtained solution, colorless crystals of 2-(5'-acetylfuryl-2')-phenanthro-/9,10/-oxazole are precipitated therefrom.

Found, %: C, 77.31; H, 4.10; N, 4.48 Calculated, %: C, 77.10; H, 3.93; N, 4.28

EXAMPLE 6

Preparing 2-(5'-carboxyfuryl-2')-phenanthro-/9,10/-oxazole

In a flask provided with a reflux condenser, 1 mmole of 9,10-phenanthraquinonimine is dissolved in 20 ml of ethanol, whereupon there are added thereto consecutively 1.2 mmole of piperidine and 1.2 mmole of 5-carboxyfurfural. The resultant mixture is boiled for 1.75 hours.

Upon termination of the reaction, 50-percent of the ethanol is distilled off from the reaction mixture and the remaining part of the latter is cooled to let the product precipitate, the precipitate is washed with ether and recrystallized from acetic acid with the use of activated charcoal to obtain colorless crystals of 2-(5'-carboxyfuryl-2')-phenanthro-/9,10/-oxazole.

Found, %: C, 72.73; H, 3.41; N, 4.36 Calculated, %: C, 72.95; H, 3.34; N, 4.25.

EXAMPLE 7

Preparing 2,5-(bis-phenanthro-/9,10/-oxazolyl-2')-furan

In a flask provided with a reflux condenser, there are dissolved under heating 2 mmole of 9,10-phenanthraquinonimine in 30 ml of ethanol, whereupon are added thereto in succession 1.2 mmole of 5-formylfurfural and 2.4 mmole of piperidine. The resultant mixture is boiled for 40 minutes and cooled. The precipitated reaction product is filtered out, washed with ethanol and crystallized from dimethylformamide to obtain light-green crystals of 2,5-(bis-phenanthro-/9,10/-oxazolyl-2')-furan.

Found, %: C, 81.3; H, 3.63; N, 5.43 Calculated, %: C, 81.27; H, 3.58; N, 5.58.

The luminescent characteristics and the melting point in degrees Centigrade are given in the Table below. Luminescence spectra were set down when activated with UV light with $\lambda_{max}=365$ nm as against a spectrophotometer. Quantum yields of luminescence were measured by comparing with standard anthracene solutions in ethanol ($\phi_f=0.22$) and in chloroform ($\phi_f=0.1$). All data hold true of experiments conducted in a medium of ethanol.

Table

| Substance | Γ max of luminescence, cm$^{-1}$ | Quantum yield of luminescence | Luminescent color | Melting point, °C |
| --- | --- | --- | --- | --- |
| (structure) | 24900 | 0.3 | violet | 231.5 to 233 |
| (structure, Cl) | 24000 | 0.45 | violet | 206 to 208 |
| (structure, Br) | 23900 | 0.2 | indigo-violet | 203 to 204 |
| (structure, COOH) | 23700 / 24800 | 0.40 | indigo | 271 to 273 |
| (structure, COCH$_3$) | 19800 | 0.61 | greenish-blue | 192 to 194 |

Table-continued
| Substance | Γ max of luminescence, cm⁻¹ | Quantum yield of luminescence | Luminescent color | Melting point, °C |
|---|---|---|---|---|
| 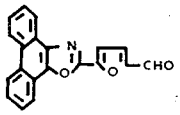 | 19600 | 0.58 | light-green | 197 to 198 |
| 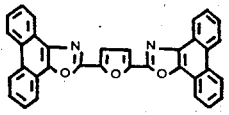 | 20400 21700 22700 | 0.4[r] | light-blue | 347 to 350 |
[r] With chloroform as a solvent.
What is claimed is:
1. A compound of the formula:
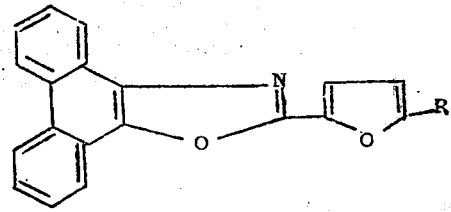
where R = CHO, COCH$_3$, COOH, or
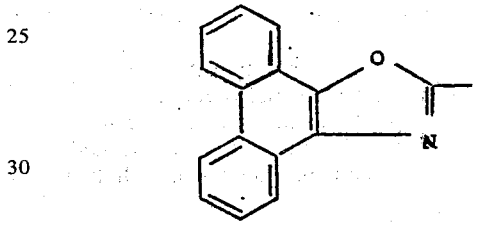
* * * * *